United States Patent
Dec et al.

(10) Patent No.: US 9,737,346 B2
(45) Date of Patent: Aug. 22, 2017

(54) REDUCTION SLEEVE

(71) Applicant: DEPUY SYNTHES PRODUCTS, INC., Raynham, MA (US)

(72) Inventors: Brian Dec, Exton, PA (US); David S. Rathbun, Gap, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/134,411

(22) Filed: Apr. 21, 2016

(65) Prior Publication Data

US 2016/0228161 A1    Aug. 11, 2016

Related U.S. Application Data

(63) Continuation of application No. 14/161,732, filed on Jan. 23, 2014, now Pat. No. 9,339,310, which is a
(Continued)

(51) Int. Cl.
*A61B 17/70* (2006.01)
*A61B 17/56* (2006.01)

(52) U.S. Cl.
CPC ...... *A61B 17/7085* (2013.01); *A61B 17/7032* (2013.01); *A61B 17/7074* (2013.01); *A61B 17/7091* (2013.01); *A61B 2017/567* (2013.01)

(58) Field of Classification Search
CPC ............ A61B 17/7074; A61B 17/7076; A61B 17/7077; A61B 17/7079; A61B 17/708;
(Continued)

(56) References Cited

U.S. PATENT DOCUMENTS

| 5,672,176 A * | 9/1997 | Biedermann | ...... A61B 17/7037 606/271 |
| 6,540,748 B2 | 4/2003 | Lombardo | |
(Continued)

*Primary Examiner* — Lynnsy Summitt
(74) *Attorney, Agent, or Firm* — Nutter McClennen & Fish LLP

(57) ABSTRACT

A reduction sleeve for facilitating insertion of a spinal rod into a rod-receiving channel formed in a bone fixation element. The reduction sleeve may include a through-bore sized and configured to receive the bone fixation element and a substantially transverse channel sized and configured to receive the spinal rod. The channel being substantially aligned with the rod-receiving channel formed in the bone fixation element so that, once the bone fixation element has been inserted into the reduction sleeve, the spinal rod can pass through the aligned channels. The reduction sleeve may also include at least one break-off point or region for facilitating breaking and removal of the reduction sleeve once the spinal rod has been clamped into the rod-receiving channel of the bone fixation element. The reduction sleeve may also include a plurality of threads formed thereon for engaging a reduction instrument, an alignment mechanism so that the bone fixation element can only be inserted into the reduction sleeve when the rod-receiving channels are aligned, and an inwardly projecting protrusion formed on the inner surface of the reduction sleeve so that, once inserted, the projection contacts a top surface formed on the bone fixation element.

22 Claims, 11 Drawing Sheets

Related U.S. Application Data continuation of application No. 11/835,159, filed on Aug. 7, 2007, now Pat. No. 8,663,292.

(60) Provisional application No. 60/839,448, filed on Aug. 22, 2006.

(58) Field of Classification Search
CPC ............ A61B 17/7082; A61B 17/7083; A61B 17/7085; A61B 17/7086; A61B 17/7088; A61B 17/7089; A61B 17/7091; A61B 2019/307
See application file for complete search history.

(56) References Cited

U.S. PATENT DOCUMENTS

| | | | |
|---|---|---|---|
| 6,641,586 B2 | 11/2003 | Varieur | |
| 7,846,093 B2 * | 12/2010 | Gorek | A61B 1/32 600/206 |
| 7,854,751 B2 * | 12/2010 | Sicvol | A61B 17/7091 606/246 |
| 8,177,817 B2 * | 5/2012 | Fallin | A61B 17/7074 606/246 |
| 8,298,138 B2 * | 10/2012 | Gorek | A61B 1/32 600/206 |
| 8,663,292 B2 | 3/2014 | Dec et al. | |
| 9,339,310 B2 | 5/2016 | Dec et al. | |
| 2004/0162560 A1 | 8/2004 | Raynor et al. | |
| 2004/0176763 A1 | 9/2004 | Foley et al. | |
| 2004/0260283 A1 | 12/2004 | Wu et al. | |
| 2005/0065517 A1 * | 3/2005 | Chin | A61B 17/3421 606/86 A |
| 2005/0131408 A1 * | 6/2005 | Sicvol | A61B 17/7091 606/86 A |
| 2006/0030861 A1 | 2/2006 | Simonson et al. | |
| 2006/0058794 A1 | 3/2006 | Jackson | |
| 2006/0074445 A1 | 4/2006 | Gerber et al. | |
| 2006/0083603 A1 | 4/2006 | Jackson | |
| 2006/0111712 A1 * | 5/2006 | Jackson | A61B 17/7037 606/914 |
| 2006/0167454 A1 * | 7/2006 | Ludwig | A61B 17/7088 606/86 A |
| 2006/0247630 A1 * | 11/2006 | Iott | A61B 17/701 606/86 A |
| 2006/0293693 A1 * | 12/2006 | Farr | A61B 17/7085 606/104 |
| 2007/0106123 A1 * | 5/2007 | Gorek | A61B 1/32 600/210 |
| 2007/0156143 A1 | 7/2007 | Lancial | |
| 2007/0270842 A1 * | 11/2007 | Bankoski | A61B 17/7076 606/86 A |
| 2008/0051794 A1 | 2/2008 | Dec et al. | |
| 2008/0234739 A1 | 9/2008 | Hudgins et al. | |
| 2014/0135854 A1 | 5/2014 | Dec et al. | |

* cited by examiner

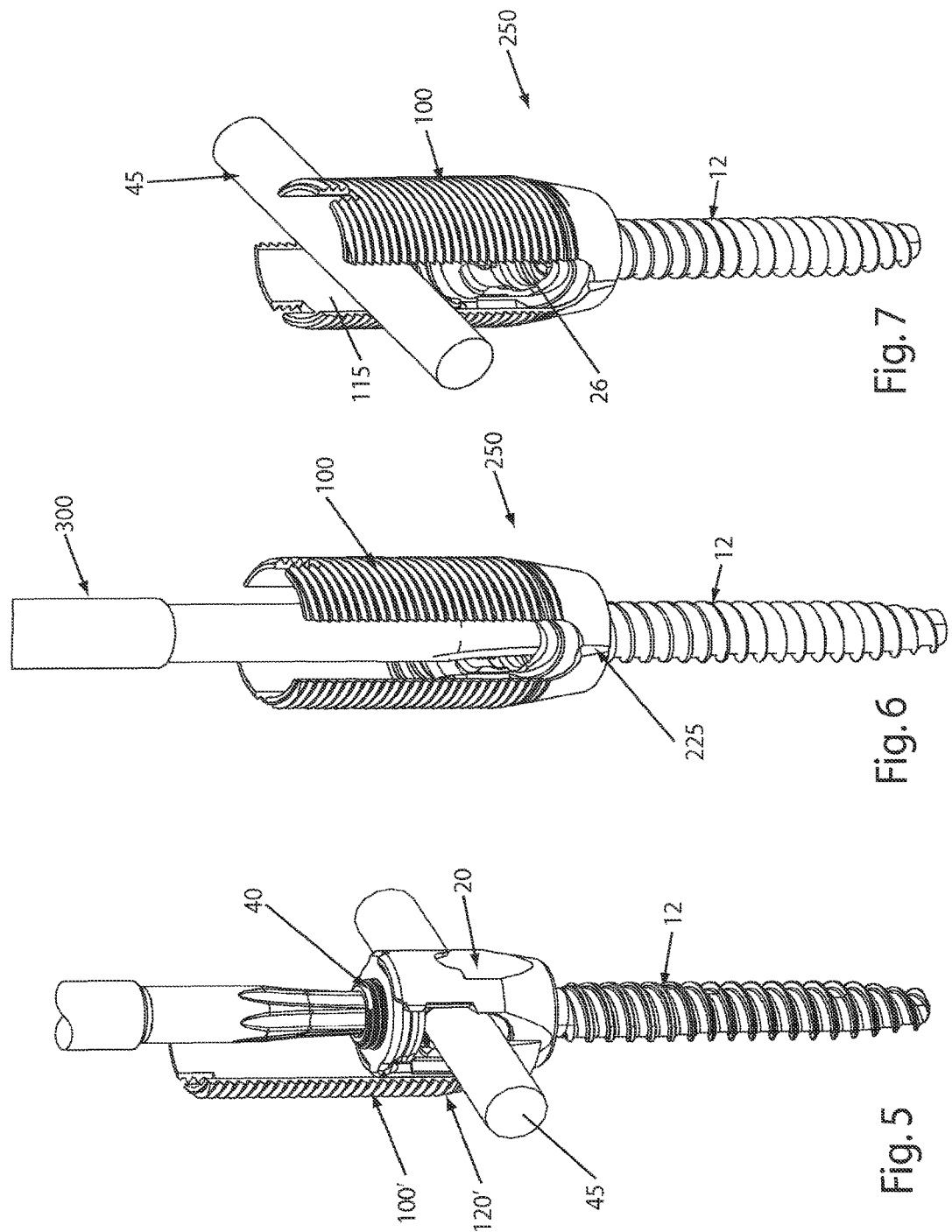

REDUCTION SLEEVE

CROSS REFERENCE TO RELATED APPLICATION

This application is a continuation of U.S. application Ser. No. 14/161,732, filed on Jan. 23, 2014, which is a continuation of U.S. application Ser. No. 11/835,159, filed on Aug. 7, 2007 (now U.S. Pat. No. 8,663,292), which claims priority to U.S. provisional patent application Ser. No. 60/839,448, filed Aug. 22, 2006, each of which is hereby incorporated by reference in its entirety.

FIELD OF THE INVENTION

The invention relates to a reduction sleeve, more specifically a reduction sleeve for facilitating insertion of a longitudinal spinal rod into a rod-receiving channel formed in a bone fixation element.

BACKGROUND OF THE INVENTION

It is often necessary due to various spinal disorders to surgically correct and stabilize spinal curvatures, or to facilitate spinal fusion. Numerous systems for treating spinal disorders have been disclosed. One known method involves a pair of elongated members, typically spinal rods, longitudinally placed on the posterior spine on either side of spinous processes of the vertebral column. Each rod is attached to various vertebra along the length of the spine by way of vertebra engaging bone fixation elements. The bone fixation elements commonly include a U-shaped rod-receiving channel for receiving the longitudinal spinal rod therein. Moreover, the rod-receiving channel often includes means for receiving a set screw or closure cap to subsequent clamp and fix the position of the spinal rod with respect to the bone fixation element. With this method, the spinal rod(s) may be shaped to maintain the vertebrae in such an orientation as to correct the spinal disorder at hand (e.g., to straighten a spine having abnormal curvature). Additionally or alternatively, the bone fixation elements may be spaced along the rods(s) to compress or distract adjacent vertebrae.

Surgeons have, however, often encountered considerable difficulty when using this method, due to problems associated with aligning the spinal rod(s) within the rod-receiving channels formed in the heads or body portion of the bone fixation elements. For example, the heads of body portions of the bone fixation elements may be out of vertical and/or horizontal alignment with one another due to the curvature of the spine or the size and shape of each vertebrae.

Thus, there exists a need for a surgical instrument and/or apparatus to help facilitate insertion of the longitudinal spinal rods into the rod-receiving channels formed in the bone fixation elements.

SUMMARY OF THE INVENTION

The present invention is directed to a reduction sleeve for facilitating insertion of a spinal rod into a rod-receiving channel formed in a bone fixation element. The reduction sleeve may include a through-bore sized and configured to receive the bone fixation element and a substantially transverse channel sized and configured to receive the spinal rod. The channel is preferably substantially aligned with the rod-receiving channel formed in the bone fixation element so that, once the bone fixation element has been inserted into the reduction sleeve, the spinal rod can pass through the aligned channels. The reduction sleeve may also include at least one break-off point or region for facilitating breaking and removal of the reduction sleeve once the spinal rod has been secured in the rod-receiving channel of the bone fixation element. The reduction sleeve may also include: (1) a plurality of threads formed thereon for engaging a reduction instrument, (2) an alignment mechanism so that the bone fixation element can only be inserted into the reduction sleeve when the rod-receiving channels are aligned, and (3) an inwardly projecting protrusion formed on the inner surface of the reduction sleeve so that, once inserted, the projection contacts a top surface formed on the bone fixation element.

In one exemplary embodiment, the reduction sleeve may include a longitudinal axis, an upper end, a lower end, an outer surface, a channel, and a through-bore extending from the upper end to the lower end, the through bore defining an inner surface. The through-bore being substantially perpendicular to the longitudinal axis and being sized and configured to receive the bone fixation element. The channel being substantially transverse to the longitudinal axis and being substantially aligned with the rod-receiving channel formed in the bone fixation element so that, once the bone fixation element has been inserted into the reduction sleeve, the spinal rod can pass through the channel formed in the reduction sleeve and the rod-receiving channel formed in the bone fixation element. The reduction sleeve preferably further including at least one break-off point or region for facilitating breaking the reduction sleeve into multiple pieces.

In another exemplary embodiment, the reduction sleeve may include a longitudinal axis, an upper end, a lower end, an outer surface, a channel, and a through-bore extending from the upper end to the lower end, the through-bore defining an inner surface. The through-bore being preferbly substantially perpendicular to the longitudinal axis and being sized and configured to receive the bone fixation element. The channel preferably being substantially transverse to the longitudinal axis and defining a pair of spaced apart arms having a top surface so that the top surface of the spaced apart arms formed in the reduction sleeve are sized and configured to extend above the top surface formed in the bone fixation element by a distance A, when the bone fixation element is inserted into the reduction sleeve. The reduction sleeve preferably also including at least one break-off point or region for facilitating breaking the reduction sleeve into multiple pieces.

In another exemplary embodiment, the reduction sleeve may include a longitudinal axis, an upper end, a lower end having a tapered surface sized and configured to contact a correspondingly tapered surface formed on a bone fixation element when the bone fixation element is inserted into the reduction sleeve, an outer surface having a plurality of threads formed thereon for engaging a reduction instrument; a through-bore extending from the upper end to the lower end, the through-bore defining an inner surface, the inner surface having an inwardly projecting protrusion formed thereon, and a channel. The through-bore being substantially perpendicular to the longitudinal axis and being sized and configured to receive the bone fixation element. The channel being substantially transverse to the longitudinal axis and defining a pair of spaced apart arms having a top surface. The reduction sleeve may further include at least one break-off point or region for facilitating breaking the reduction sleeve into multiple pieces. The inwardly projecting protrusion formed on the inner surface of the reduction sleeve is sized and configured to contact the top surface of the bone fixation element, once the bone fixation element has been inserted into the reduction sleeve, so that the bone fixation element can be secured within the reduction sleeve in-between the tapered surface formed in the lower end of the reduction sleeve and the inwardly projecting protrusion.

The reduction sleeve may include a pair of break-off points or regions formed in the lower end of the reduction sleeve beneath the channel formed in the reduction sleeve. The channel formed in the reduction sleeve may define a pair of spaced apart arms joined by a bridge member so that the reduction sleeve is generally in the form of a U-shaped member, the break-off point or region being formed in the bridge member. The break-off point or region may preferably be formed beneath the channel and extends vertically from the channel to the lower end of the reduction sleeve.

The rod-receiving channel formed in the bone fixation element preferably defines a pair of spaced apart arms and the channel formed in the reduction sleeve preferably defines a pair of spaced apart arms, the spaced apart arms being substantially aligned with one another once the bone fixation element has been inserted into the reduction sleeve.

The reduction sleeve may further include a plurality of threads for engaging a reduction instrument. The plurality of threads preferably being formed on the outer surface of the reduction sleeve.

The lower end of the reduction sleeve preferably includes a tapered surface sized and configured to receive a correspondingly tapered surface formed on the bone fixation element.

Preferably, once inserted, the bone anchor extends through the lower end of the reduction sleeve such that the bone anchor may be moveable with respect to the bone fixation element and with respect to the reduction sleeve.

The reduction sleeve may also include an alignment mechanism so that the bone fixation element can only be inserted into the reduction sleeve when the rod-receiving channel formed in the bone fixation element is aligned with the channel formed in the reduction sleeve. The alignment mechanism preferably is sized and configured as an alignment flat formed in the lower end of the reduction sleeve, the alignment flat being sized and configured to contact a corresponding flat formed on the bone fixation element.

The reduction sleeve may also include a protrusion formed on the inner surface thereof, the protrusion projecting inward from the inner surface so that, once inserted, the projection contacts a top surface formed on the bone fixation element. Once inserted, the bone fixation element preferably is secured within the reduction sleeve in-between the lower end of the reduction sleeve and the protrusion.

The bone anchor is preferably sized and configured to engage a patient's vertebra.

The reduction sleeve of claim preferably has the shape of a sleeve or tubular member.

The transverse channel preferably extends from the upper end towards the lower end.

BRIEF DESCRIPTION OF THE DRAWINGS

The system is explained in even greater detail in the following exemplary drawings. The drawings are merely exemplary to illustrate the structure of preferred devices and certain features that may be used singularly or in combination with other features. The invention should not be limited to the embodiments shown.

FIG. 5 is an alternate exemplary embodiment of a reduction sleeve;

FIG. 6 is a perspective view of the reduction sleeve and bone fixation element of FIG. 4 being engaged by a screwdriver or other similar type device;

FIG. 7 is a perspective view of the reduction sleeve and bone fixation element of FIG. 4 with a longitudinal spinal rod shown therein;

DETAILED DESCRIPTION

Certain exemplary embodiments of the invention will now be described with reference to the drawings. In general, such embodiments relate to a reduction sleeve, by way of non-limiting example, a reduction sleeve for use in posterior spinal fixation to facilitate insertion of a longitudinal spinal rod in a rod-receiving channel formed in a bone fixation element. The invention may have other applications and uses and should not be limited to the structure or use described and illustrated. As will be described in greater detail below, the reduction sleeve may include a vertical through-bore sized and configured to receive a bone fixation element and a transverse channel sized and configured to receive a longitudinal spinal rod. The reduction sleeve may also include a break-off point and/or region so that after the longitudinal spinal rod has been inserted in the rod-receiving channel of the bone fixation element, the reduction sleeve can be removed from the patient's body leaving in place the bone fixation element and spinal rod.

While the reduction sleeve will be described as and may generally be used in the spine (for example, in the lumbar, thoracic or cervical regions), those skilled in the art will appreciate that the reduction sleeve may be used for fixation of other parts of the body such as, for example, joints, long bones or bones in the hand, face, feet, extremities, cranium, etc.

As will be described in greater detail below, the reduction sleeve may be used to facilitate insertion of a longitudinal spinal rod into a rod-receiving channel formed in a bone fixation element. It should be understood that the spinal rod may include, but not limited to, a solid rod, a non-solid rod, a flexible or dynamic rod, etc. It should be understood that the reduction sleeve is not limited in use to any particular type of spinal rod.

Figure 1:
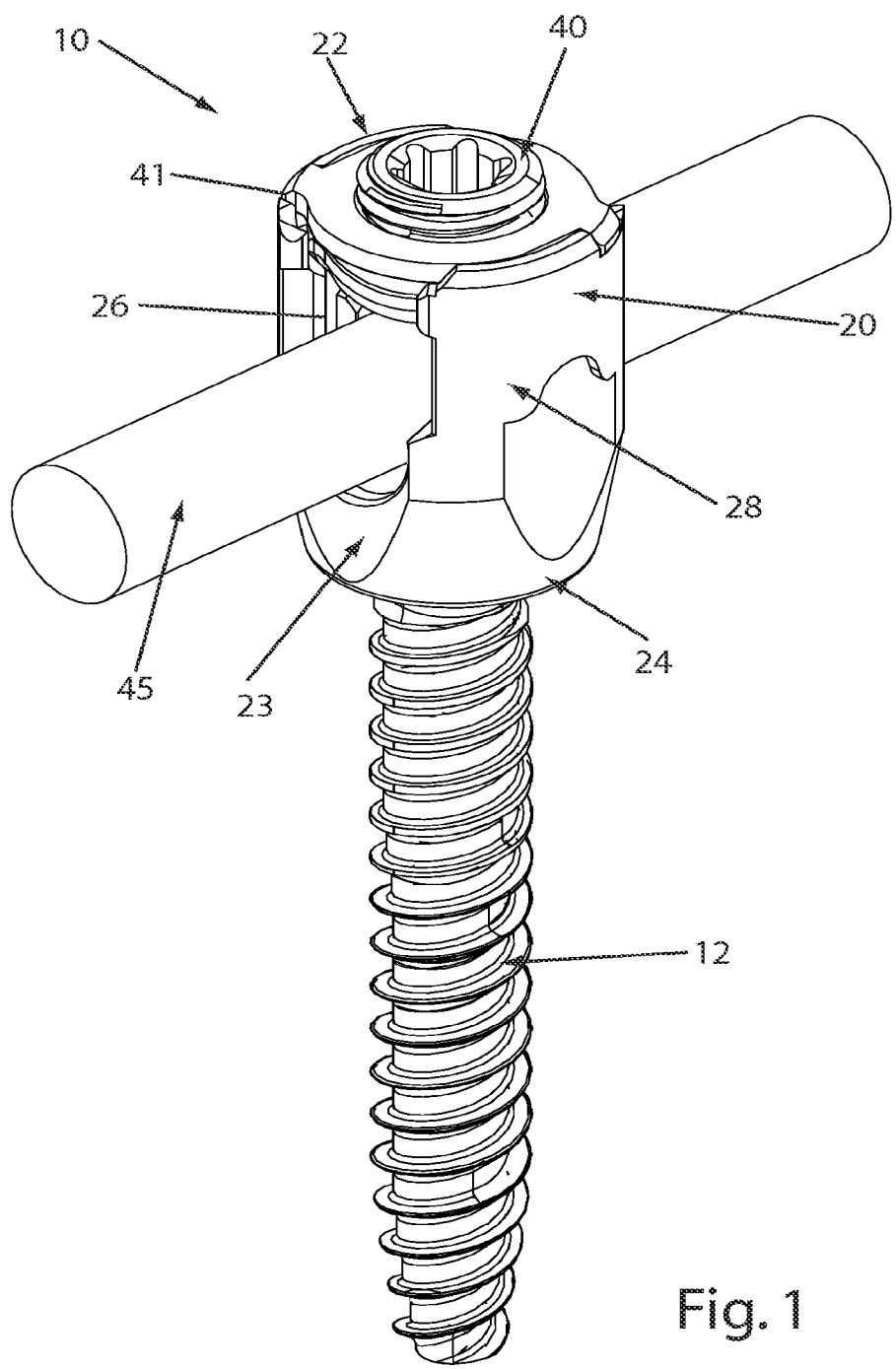
FIG. 1 is a perspective view of a prior art bone fixation element.
Figure 2:
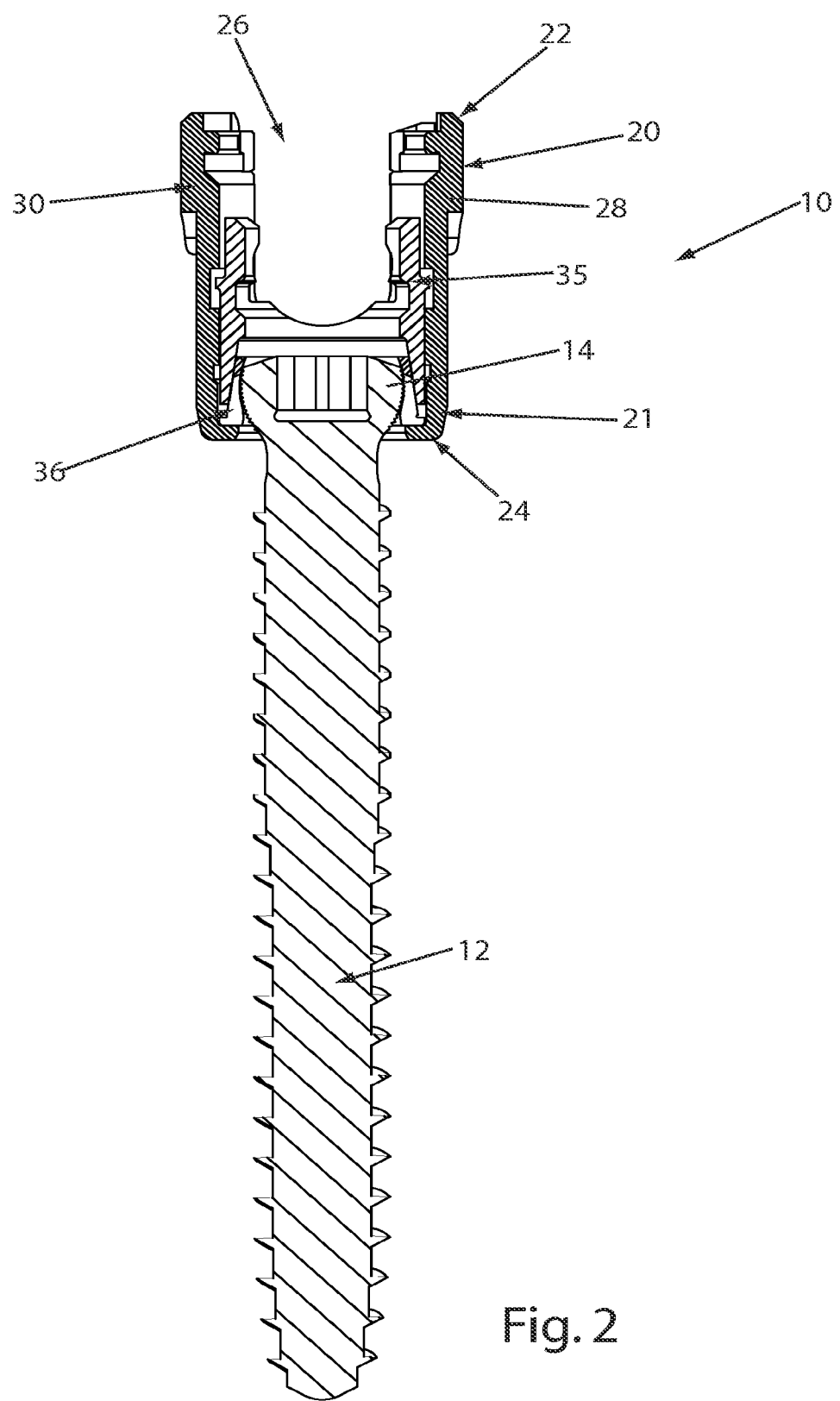
FIG. 2 is a cross-sectional view of the prior art bone fixation element shown in FIG. 1.

As will be described in greater detail below, the reduction sleeve may be used in conjunction with a bone fixation element in order to assist the surgeon with insertion of the spinal rod into the rod-receiving channel formed in the bone fixation element. As generally understood by one of ordinary skill in the art, it should be understood that bone fixation element is used generally and may include, but are not limited to, poly-axial or mono-axial pedicle screws, hooks (both mono-axial and poly-axial) including pedicle hooks, transverse process hooks, sublaminar hook, or other fasteners, clamps or implants. One example of a bone fixation element is the Pangea™ pedicle screw system distributed by Synthes® (U.S.A.). As shown in FIGS. 1 and 2, an exemplary embodiment of a bone fixation element 10 is shown. As shown, the bone fixation element 10 may include a bone anchor 12 (shown as a bone screw) having an enlarged head portion 14, a body portion 20 (shown as a top loading body portion) having an upper end 22, a lower end 24, a rod-receiving channel 26 (shown as a top loading U-shaped rod-receiving channel) defining a pair of spaced apart arms 28, 30, a sleeve 35 and a collet 36 slidably disposed within the body portion 20, at least a portion of the collet 36 being slidably disposed within the sleeve 35, and a set screw or closure cap 40. In use, the enlarged end portion 14 of the bone anchor 12 may be separate from and be disposed within the lower end 24 of the body portion 20 so that the bone anchor 12 can poly-axial rotate with respect to the body portion 20. Alternatively, the bone anchor or hook 12 may be formed integral with the body portion 20 to form a monolithic structure which is sometimes referred to as a mono-axial pedicle screw or hook.

Once the spinal rod 45 is inserted into the rod-receiving channel 26, the surgeon can secure the position of the rod 45 with respect to the body portion 20 and the position of the bone anchor 12 with respect to the body portion 20 by engaging, for example, by rotating the set screw or closure cap 40. Rotation of the set screw or closure cap 40 may cause the set screw or closure cap 40 to exert a downward force onto the spinal rod 45, which is received within the rod-receiving channel 26, which, in turn, causes the rod 45 to exert a downward force onto the sleeve 35 with causes the sleeve 35 to move with respect to the collet 36, which in turn causes the collet 36 to compress around the enlarged head portion 14 of the bone anchor 12 thereby securing the position of the bone anchor 12 with respect to the body portion 20. In addition, rotation of the set screw or closure cap 40 may cause the spinal rod 45 to be sandwiched in-between the set screw or closure cap 40 and the sleeve 35 thereby securing the position of the rod 45 with respect to the body portion 20.

The bone fixation element 10 may be sized and configured with a low profile so that the height of the bone fixation element 10 is minimized in order to reduce the amount of associated trauma. That is, preferably, the overall height of the body portion 20 is minimized so that, once engaged, the bone fixation element 10 does not extend anymore than is necessary above the patient's vertebra. The height of the body portion may be between about 10 mm and 25 mm and, preferably, between about 12 mm and 17 mm. It should be understood however that the reduction sleeve is not limited in use to any particular type of bone fixation element.

Figure 3:
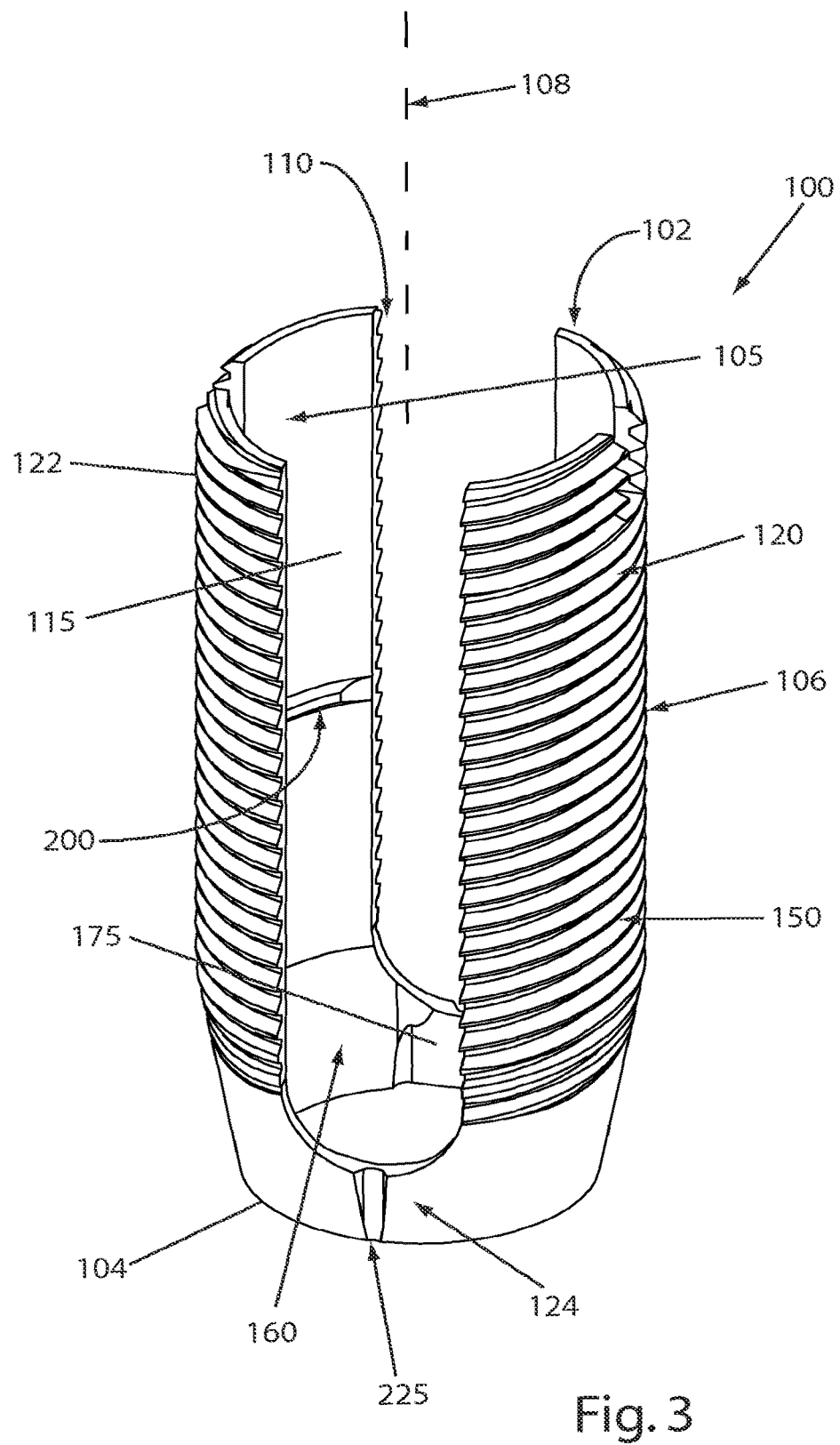
FIG. 3 is a perspective view of an exemplary embodiment of a reduction sleeve.

As shown in FIG. 3, the reduction sleeve 100 may be generally in the shape of a sleeve or tubular member having an upper end 102, a lower end 104, an inner surface 105, an outer surface 106 and a longitudinal axis 108. The reduction sleeve 100 may also include a through-bore 110 extending from the upper end 102 to the lower end 104, the through-bore 110 being generally orientated parallel to the longitudinal axis 108 for receiving a bone fixation element, such as bone fixation element 10, as shown in FIGS. 1 and 2. However, the through-bore can be at an angle with respect to the longitudinal axis 108 of the reduction sleeve 100. The reduction sleeve 100 may also include a channel 115 that preferably extends from the upper end 102 towards the lower end 104, the channel 115 being generally orientated transverse to the longitudinal axis 108 for receving the longitudinal spinal rod, such as spinal rod 45, as shown in FIGS. 1 and 2. However, the transverse channel can be at any angle with respect to the longitudinal axis 108 of the reduction sleeve 100. The channel 115 defining a pair of spaced apart arms 120, 122 which may be joined together in the lower end 104 by a bridge member 124. In this manner, the reduction sleeve 100 may be generally in the form of a U-shaped member.

As shown, the reduction sleeve 100 may also include a plurality of threads 150 formed on the outer surface 106 of the spaced apart arms 120, 122 for threadably engaging a reduction instrument, as will be described in greater detail below. Preferably, the threads 150 begin at or near the upper end 102 and extend substantially the entire length of the spaced apart arms 120, 122 and/or the entire length of the channel 115. Alternatively, the reduction sleeve 100 may be formed with internal threads 150 formed on the inner surface 105 of the spaced apart arms 120, 122. In addition, it should be understood that other forms of engagement between the reduction sleeve 100 and reduction instrument are contemplated, such as, for example, a snap-fit type connection wherein the spaced apart arms 120, 122 may include a plurality of ridges for engaging a projection formed on the reduction instrument.

As previously described, the bone fixation element 10 may be sized and configured with a low profile so that the height of the bone fixation element 10, and in particular the height of the body portion 20, is minimized in order to reduce the overall amount of associated trauma. One disadvantage of minimizing the height of the bone fixation element 10 is that the spinal rod 45 may be vertically and/or horizontally offset with respect to the rod-receiving channel 26 formed in the bone fixation element 10 making it more difficult for the surgeon to insert and clamp the spinal rod 45 into the rod-receiving channel 26 of the bone fixation element 10. To this end, incorporation of the reduction sleeve 100 may enable a surgeon to temporary extend the overall height of the bone fixation element 10 to facilitate insertion of the spinal rod 45 into the rod-receiving channel 26 of the bone fixation element 10. Thereafter, once inserted, the reduction sleeve 100 may be removed and/or disposed leaving behind the bone fixation element 10 and clamped spinal rod 45. The reduction sleeve 100 may have a height of about 20 mm to 60 mm and, preferably, between about 28 mm and 35 mm to help facilitate insertion of the spinal rod 45 into the rod-receiving channel 26 of the bone fixation element 10.

Figure 4:
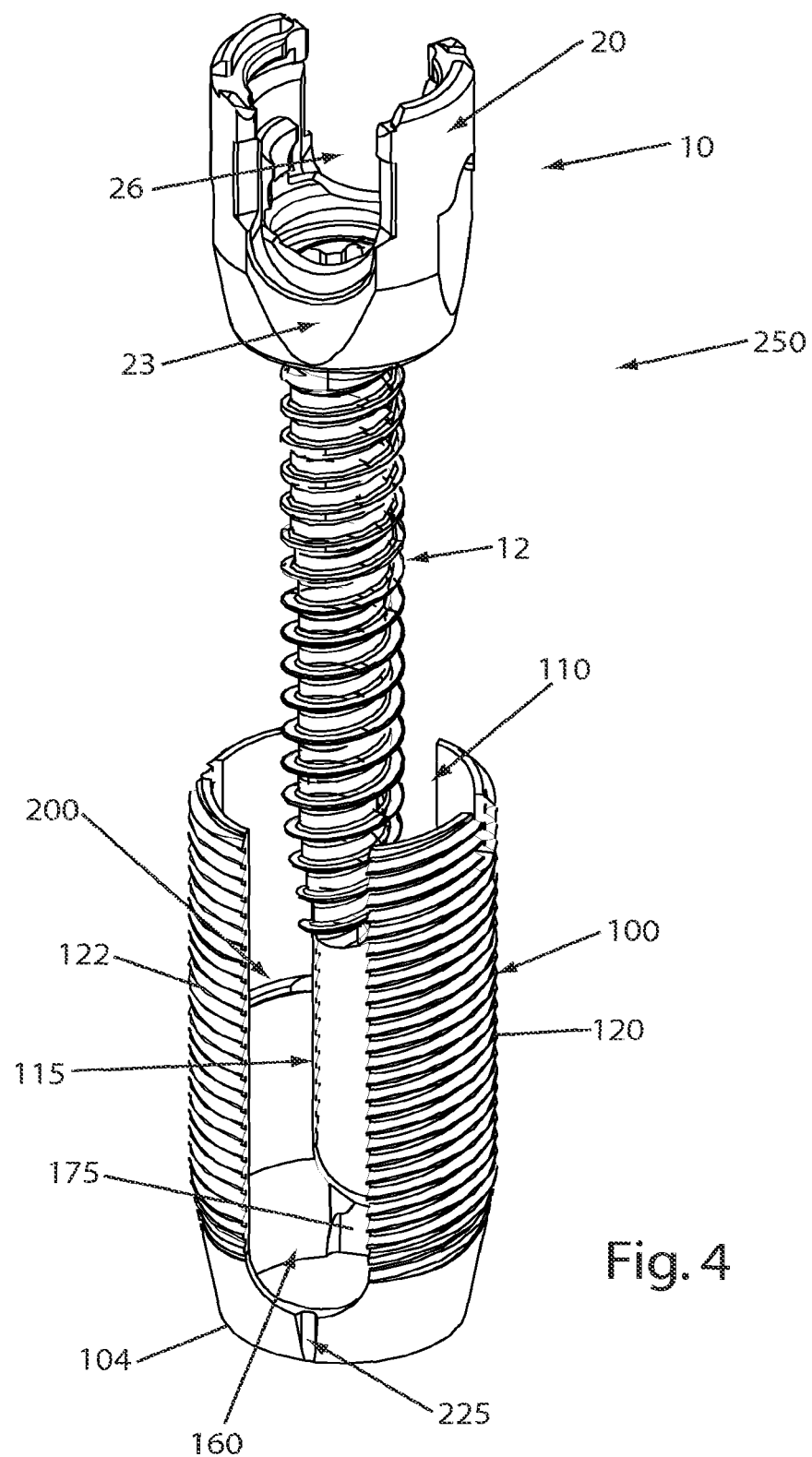
FIG. 4 is a perspective view of a bone fixation element being inserted into the reduction sleeve of FIG. 3.

As shown in FIG. 3, the lower end 104 of the reduction sleeve 100 may include a tapered surface 160 for receiving the body portion 20 of the bone fixation element 10 such that, as best shown in FIG. 4, as the bone fixation element 10 is inserted into the through-bore 110 of the reduction sleeve 100, the bone anchor 12 passes through the reduction sleeve 100 so that it may engage the patient's vertebra while the body portion 20 of the bone fixation element 10 includes a surface 21, preferably a corresponding tapered lower surface, sized and configured to be received within the lower end 104 of the reduction sleeve 100. In this manner, preferably, the bone anchor 12 may be poly-axially rotated with respect to the body portion 20 of the bone fixation element 10 even after the bone fixation element 10 is inserted into the reduction sleeve 100. Preferably, the tapered surface 160 formed on the lower surface 104 of the reduction sleeve 100 and the corresponding tapered surface 21 formed on the bone fixation element 10 are sized and configured within tight tolerances to help facilitate retention of the bone fixation element 10 within the reduction sleeve 100. The tapered surface 21 may have a tapered angle of approximately 10 degrees with a height between about 5 mm and about 6 mm.

In use, the rod-receiving channel 26 formed in the body portion 20 of the bone fixation element 10 may be sized and configured to align with the channel 115 formed in the reduction sleeve 100 so that the longitudinal spinal rod 45 may pass completely through the reduction sleeve 100 and bone fixation element 10 even after the bone fixation element 10 has been inserted into the reduction sleeve 100. Preferably, the lower end 104 of the reduction sleeve 100 may include an alignment mechanism so that the bone fixation element 10 can only be inserted into the reduction sleeve 100 when the rod-receiving channels 26, 115 are aligned. For example, as best shown in FIGS. 3 and 4, the lower end 104 of the reduction sleeve 100 may include an alignment flat 175 that may be sized and configured to engage a corresponding flat 23 formed on the body portion 20 of the bone fixation element 10. As will be generally understood by one of ordinary skill in the art, other alignment mechanism may be used, including, for example, one of the reduction sleeve 100 and bone fixation element 10 may include a projection for engaging a groove formed on the other of the reduction sleeve 100 and bone fixation element 10.

As best shown in FIG. 3, the reduction sleeve 100 may also include a ledge or protrusion 200 formed and extending inwardly from the inner surface 105 of the spaced apart arms 120, 122. As will be generally appreciated by one of ordinary skill in the art, during insertion of the bone fixation element 10 into the reduction sleeve 100, the inwardly protruding ledge or protrusion 200 will cause the spaced apart arms 28, 30 formed on the body portion 20 of the bone fixation element 10 to deflect inwards until the top of the spaced apart arms 28, 30 formed on the bone fixation element 10 pass completely beyond that inwardly protruding ledge or protrusion 200. At that point, the spaced apart arms 28, 30 formed on the bone fixation element 10 will revert back to their original, upright position causing the body portion 20 of the bone fixation element 10 to be secured within the reduction sleeve 100. More particularly, the body portion 20 of the bone fixation element 10 will be secured between the inwardly protruding ledge or protrusion 200 and the tapered surface 160 formed at the lower end 104 of the reduction sleeve 100. In this manner, the reduction sleeve 100 and bone fixation element 10 may be pre-assembled by the manufacturer and/or by the surgeon prior to insertion so that the reduction sleeve 100 and bone fixation element 10 may be inserted into the patient's vertebra as a single piece. In addition, as previously described, the tapered surface 160 formed on the lower surface 104 of the reduction sleeve 100 and the corresponding tapered surface 21 formed on the bone fixation element 10 are sized and configured within tight tolerances to further secure the bone fixation element 10 within the reduction sleeve 100.

Moreover, as best shown in FIG. 3, the reduction sleeve 100 may also include one or more break-off point(s) or region(s) 225. Preferably the reduction sleeve 100 includes a pair of break off points or regions 225 located on the lower end 104 of the reduction sleeve 100 beneath the rod-receiving channel 115. That is, as shown, preferably the break-off points or regions 225 are formed beneath the channel 115 and extend vertically from the channel 115 to the lower end 104 of the reduction sleeve 100. In this manner, the break-off points or regions 225 are located at the smallest and/or weakness point of the reduction sleeve 100 making it easier for the reduction sleeve 100 to be broken, removed and/or discarded.

The break-off points or regions 225 are preferably an area of weakness formed, preferably intentionally, in the reduction sleeve 100 so that the reduction sleeve 100 will break or rupture when subjected to high stresses, such as by intentional stresses induced by the surgeon in order to break the reduction sleeve 100 into multiple pieces so that the reduction sleeve 100 can be, partially or completely, removed from the patient's body after the longitudinal spinal rod 45 has been seated and secured within the rod-receiving channel 26 of the bone fixation element 10. The break-off point 225 may be configured as a weakened region, a thinned-out area, a groove, etc. As will be appreciated by one of ordinary skill in the art, the reduction sleeve 100 may contain any number of break-off points or regions 225 located anyway on the reduction sleeve 100. Incorporation of the break-off points or regions 225 enable the reduction sleeve 100 to be discarded. That is, the break-off points or regions 225 enable the reduction sleeve 100 to be constructed as a separate and distinct part from the bone fixation element 10. This, optionally, enables the reduction sleeve 100 to be manufactured from a different and/or cheaper material as compared to the bone fixation element 10. Moreover, since the reduction sleeve 100 is broken and discarded, no sharp edges are left on the bone fixation element 10, for example, as compared to prior art bone fixation elements that incorporate integral extension areas via a break-off point or region.

Alternatively, as shown in FIG. 5, the reduction sleeve 100 may be configured as a side opening or lateral engaging reduction sleeve 100'. In this manner, the reduction sleeve 100' may be sized and configured with a single spaced apart arm 120' for engaging a reduction instrument, as will be described in greater detail below. In this embodiment, the break-off point 225 may be omitted as the reduction sleeve 100' may be preferably sized and configured to engage the bone fixation element 10 from a single side thereof, thus enabling the surgeon to engage and disengage the reduction sleeve 100' as necessary. One particular advantage of this embodiment is that the reduction sleeve 100' is not broken and/or discarded after each use but rather may be reused again during the surgery.

Referring again to FIG. 4, in use, the bone fixation element 10 may be inserted into the reduction sleeve 100 via the through-bore 110 so that preferably the body portion 20 of the bone fixation element 10 is seated between the tapered surface 160 of the lower end 104 of the reduction sleeve 100 and the inwardly projecting ledge or protrusion 200 formed on the spaced apart arms 120, 122. The bone anchor 12 extending through the lower end 104 of the reduction sleeve 100 and preferably being capable of poly-axially rotating with respect to the bone fixation element 10 and reduction sleeve 100. Moreover, preferably the rod-receiving channel 26 formed in the bone fixation element 10 may be aligned with the rod-receiving channel 115 formed in the reduction sleeve 100 so that the longitudinal spinal rod 45 is able to pass completely through the assembled device 250 (e.g., the reduction sleeve 100 with the bone fixation element 10 seated therein).

As best shown in FIG. 6, with the bone fixation element 10 secured between the inner surface 105 of the reduction sleeve 100 and the inwardly projecting ledge or protrusion 200, the assembled device 250 may be secured to a patient's body, preferably the patient's vertebra, by a screwdriver or other similar type device 300. Once engaged to the patient's vertebra, the surgeon can preferably, so long as a mono-axial bone fixation element isn't used, poly-axially rotate the body portion 20 of the bone fixation element 10 and the reduction sleeve 100 with respect to the bone anchor 12 so that the longiditudinal spinal rod 45 can be inserted into the rod-receiving channel 115 of the reduction sleeve 100. At this point, the spinal rod 45 may or may not be seated within the rod-receiving channel 26 of the bone fixation element 10, as best shown in FIG. 7.

Figure 8A:
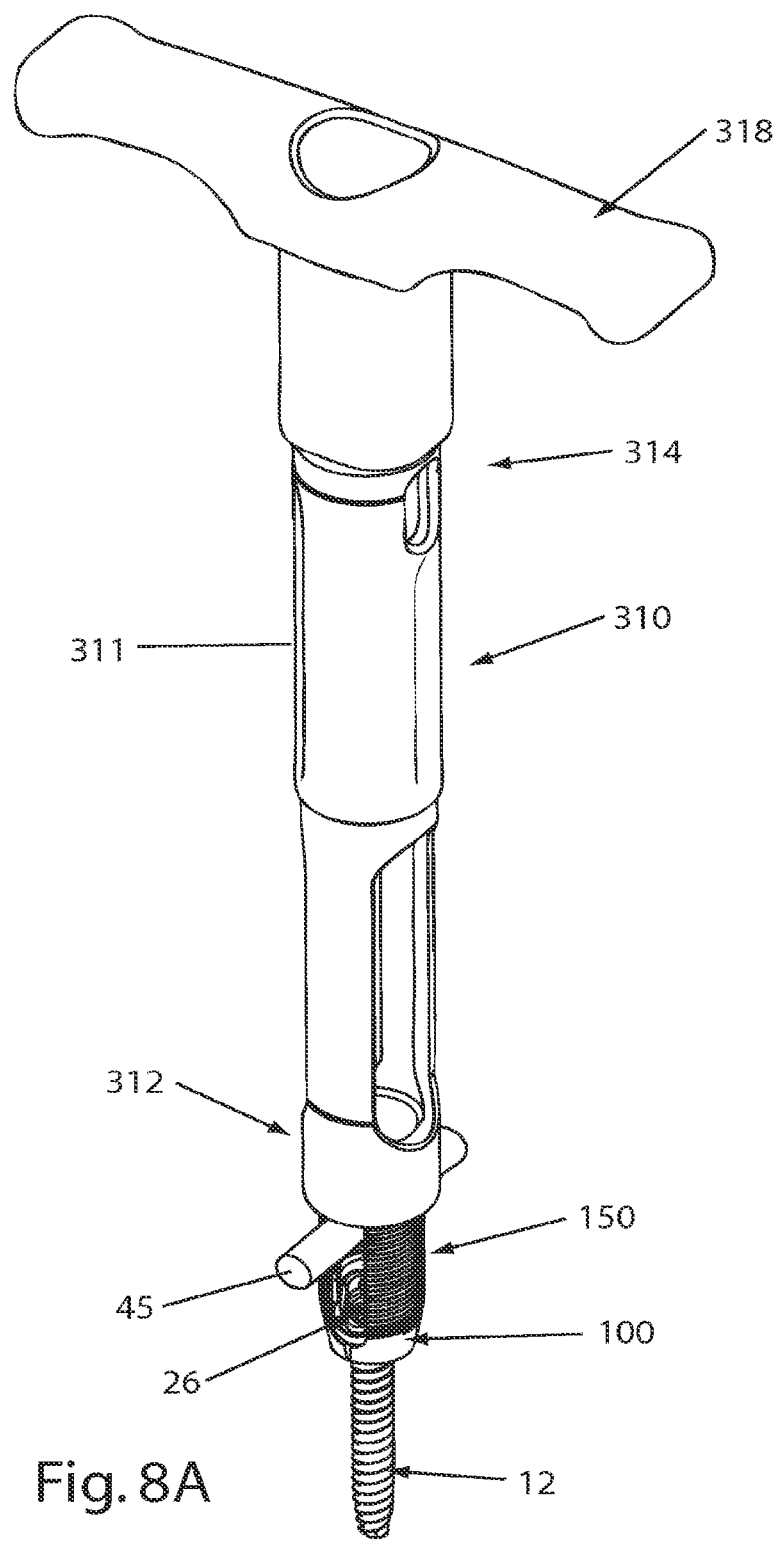
FIG. 8A is a perspective view of a reduction instrument urging the spinal rod into the reduction sleeve and bone fixation element.
Figure 8B:
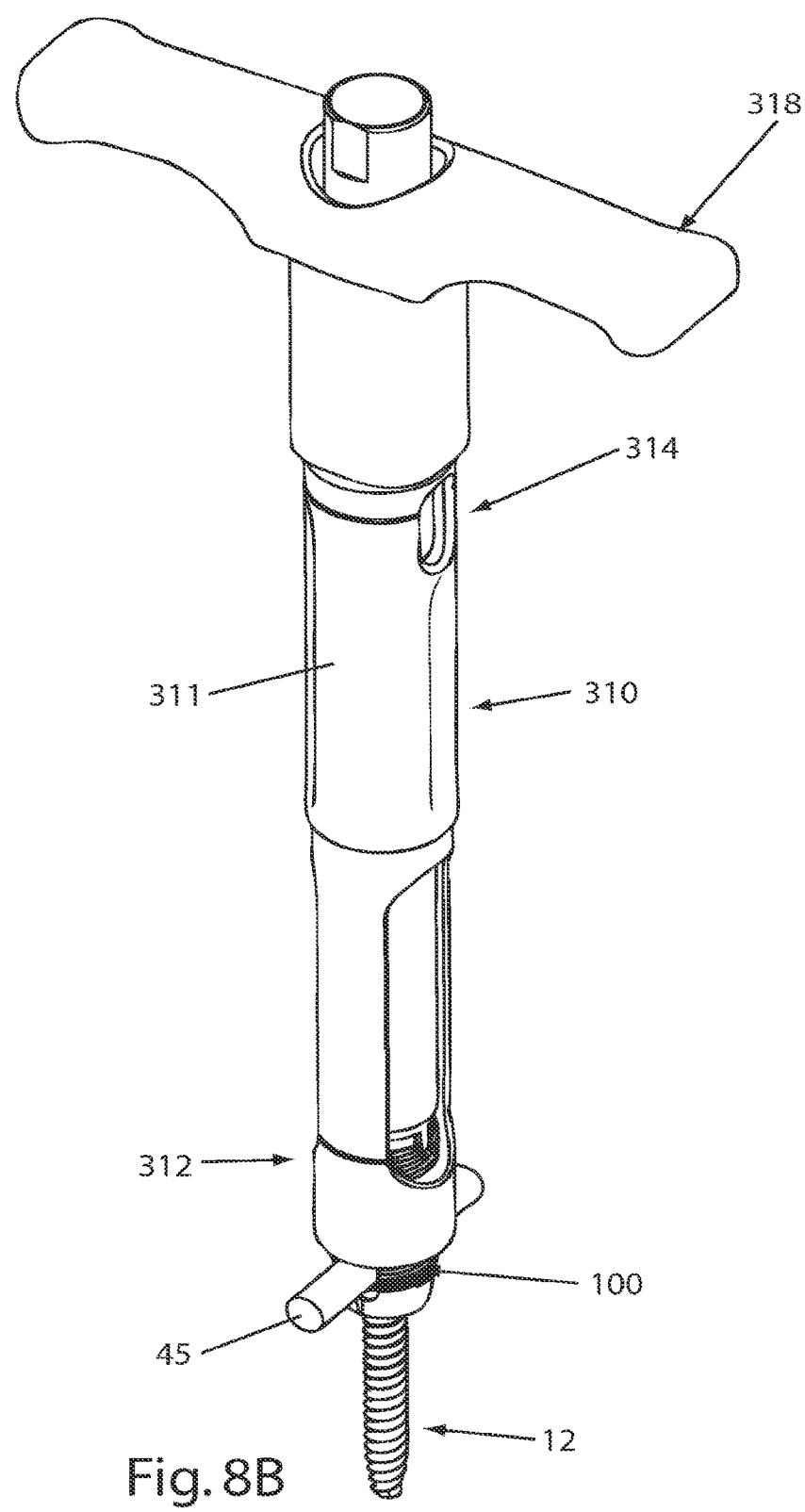
FIG. 8B is another perspective view of the reduction instrument urging the spinal rod into the reduction sleeve and bone fixation element.

Next, as best shown in FIGS. 8A and 8B, a reduction instrument 310 may be used to engage the reduction sleeve 100 in order to urge the spinal rod 45 into the rod-receiving channel 26 of the bone fixation element 10. The reduction instrument 310 may include a tube 311 having a distal end 312 and a proximal end 314, the distal end 312 may include one or more internal threads 316 for engaging the external threads 150 formed on the spaced apart arms 120, 122 of the reduction sleeve 100 such that rotation of the reduction instrument 310 causes the reduction instrument 310 to move with respect to the reduction sleeve 100, which in turn, may cause the distal end 312 of the reduction instrument 310 to contact the spinal rod 45 so that continued rotation of the reduction instrument 310 urges the rod 45 into the rod-receiving channel 26 of the bone fixation element 100. That is, rotation of the reduction instrument 310 causes the reduction instrument 310 to move with respect to the reduction sleeve 100, which, in turn, causes the distal end 312 of the reduction instrument 310 to contact the spinal rod 45 so that continued rotation of the reduction instrument 310 moves the rod 45 from a first position where the rod 45 may be in the channel 115 formed in the reduction sleeve 100 but not in the rod-receiving channel 26 of the bone fixation element 100, as shown in FIG. 8A, to a second position where the rod 45 may be located in both the channel 115 formed in the reduction sleeve 100 and the rod-receiving channel 26 of the bone fixation element 100, as shown in FIG. 8B. Alternatively, as previously described, the reduction instrument 310 may include external threads for engaging internal threads formed on the spaced apart arms 120, 122 of the reduction sleeve 100 or any other attachment means known in the art. The reduction sleeve 100 and reduction instrument 310 are preferably configured with corresponding increased thread pitch to enable faster reduction of the spinal rod 45. That is, the reduction sleeve 100 and reduction instrument 310 may be configured with corresponding increased thread pitch so that less rotation of the reduction instrument 310 is required to move the reduction instrument 310 axially with respect to the reduction sleeve 100. For example, the reduction sleeve 100 and reduction instrument 310 may be configured with an M15 thread pitch. However, as will be appreciated by one of ordinary skill in the art, any thread pitch may be used. In addition, as shown, the reduction instrument 310 may also include a handle 318, preferably a T-handle, to facilitate rotation of the reduction instrument 310.

Figure 9:
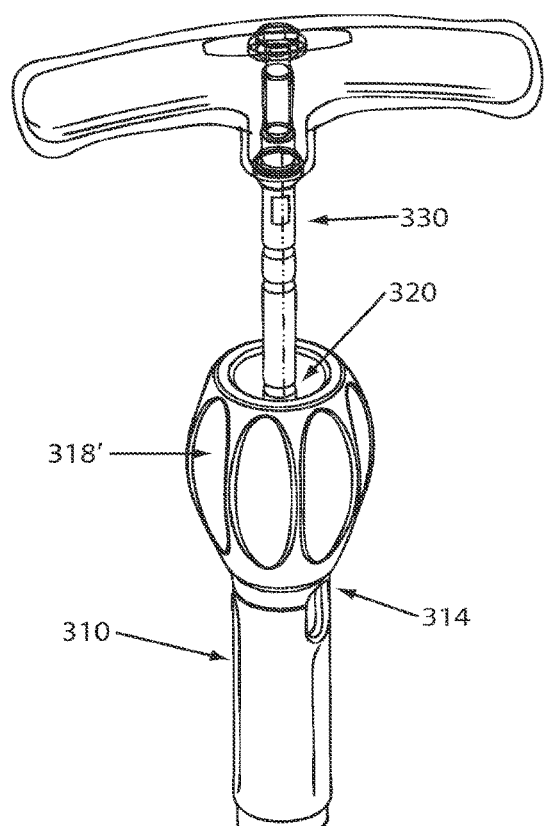
FIG. 9 is a perspective view of another exemplary embodiment of a reduction insertion and screwdriver or other similar type device.
Figure 10:
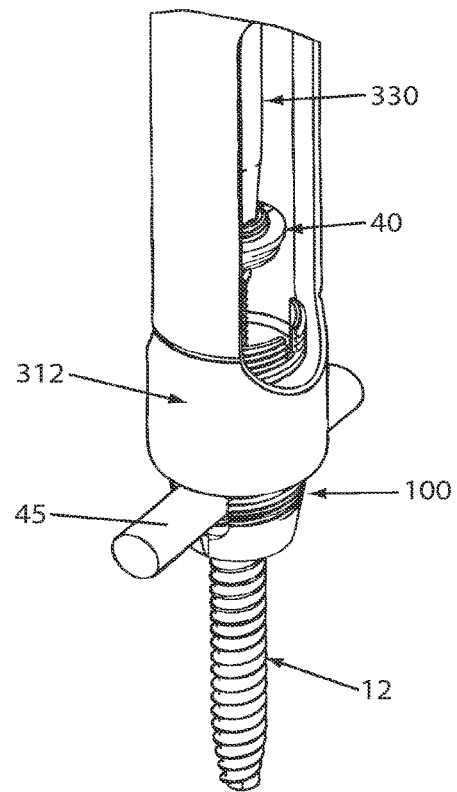
FIG. 10 is a close up, perspective view of the reduction instrument of FIG. 9 engaging the bone fixation element.

Moreover, as best shown in FIGS. 9 and 10, the reduction instrument 310 (shown here with an optionally knurled knob 318' as opposed to the T-handle 318 mentioned above) preferably includes a central bore 320 extending from the proximal end 314 to the distal end 312. The bore 320 preferably being sized and configured to receive the set screw or closure cap 40 and associated screwdriver or similar type device 330 so that once the spinal 45 has been urged into the rod-receiving channel 26 formed in the bone fixation element 10, the surgeon can clamp the spinal rod 45 within the rod-receiving channel 26 of the bone fixation element 10 by securing the set screw or closure cap 40 to the bone fixation element 10. As will be generally understood by one or ordinary skill in the art, the knurled knob 318' and T-handle 318 are easily interchangeable.

Figure 11:
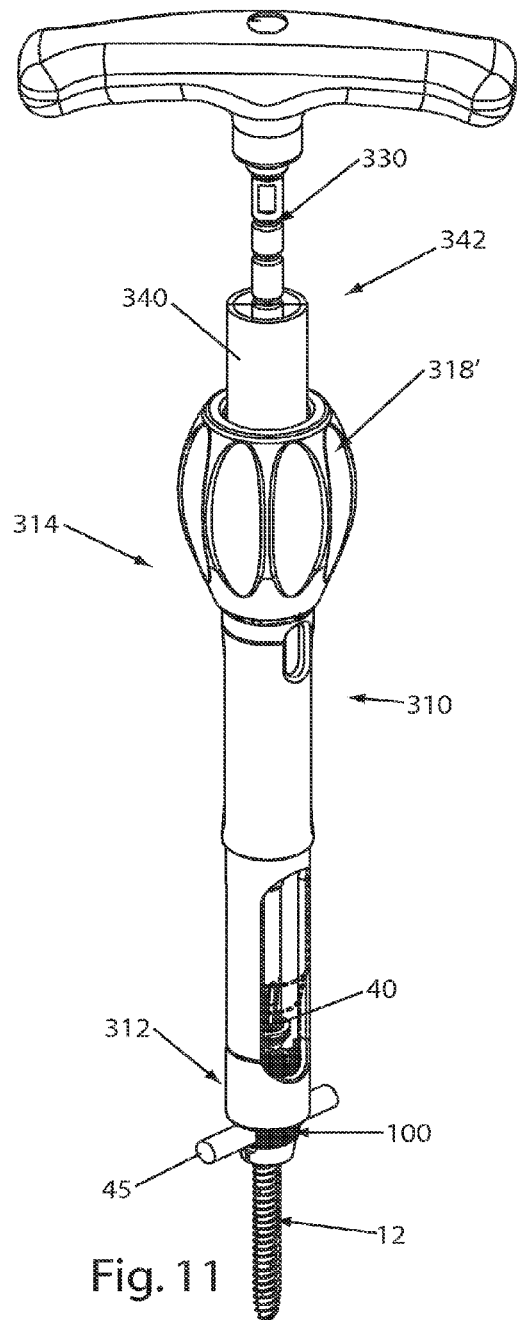
FIG. 11 is another perspective view of the reduction instrument of FIGS. 8A-10 incorporating a cap alignment tube.
Figure 12:
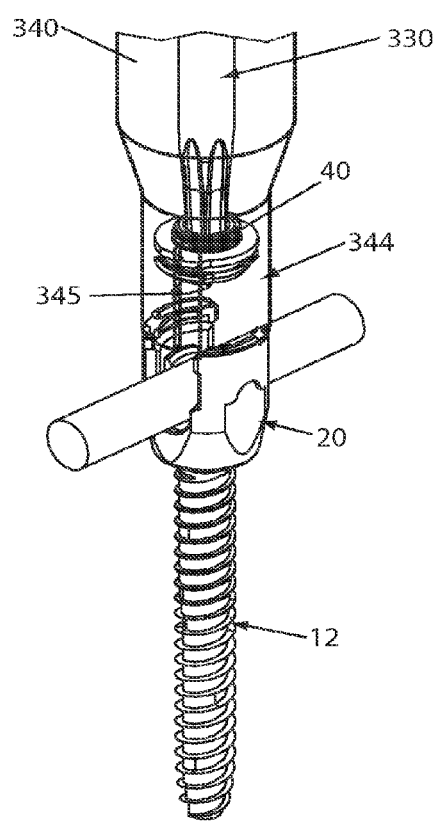
FIG. 12 is a close up, perspective view of the cap alignment tube of FIG. 11, engaging the bone fixation element.

In addition, as best shown in FIGS. 11 and 12, the central bore 320 may be sized and configured to receive an optional cap alignment tube 340. The cap alignment tube 340 may be preferably sized and configured with an alignment mechanism so that when the cap alignment tube 340 is inserted into the reduction instrument 310, the cap alignment tube 340 only permits the set screw or closure cap 40 to be inserted into the spaced apart arms 120, 122 formed on the bone fixation element 10 in proper alignment. More particularly, as shown in FIG. 12, the cap alignment tool 340 may include a plurality of slots 345 extending from a distal end 344 thereof. The slots 345 being sized and figured to receive and guide tabs 41 (as best shown in FIG. 1) extending from the set screw or closure cap 40 into engagement with the spaced apart arms 28, 30 formed on the bone fixation element 10. In addition, the cap alignment tube 340 may be preferably sized and configured to prevent the tabs 41 formed on the set screw or closure cap 40 from accidentally being dropped into the rod-receiving channel 26 formed on the bone fixation element 10. The cap alignment tool 340 may also incorporate a handle (not shown). Preferably the cap alignment tool 340 includes a handle extending from the proximal end 342 thereof.

Figures 13, 14:
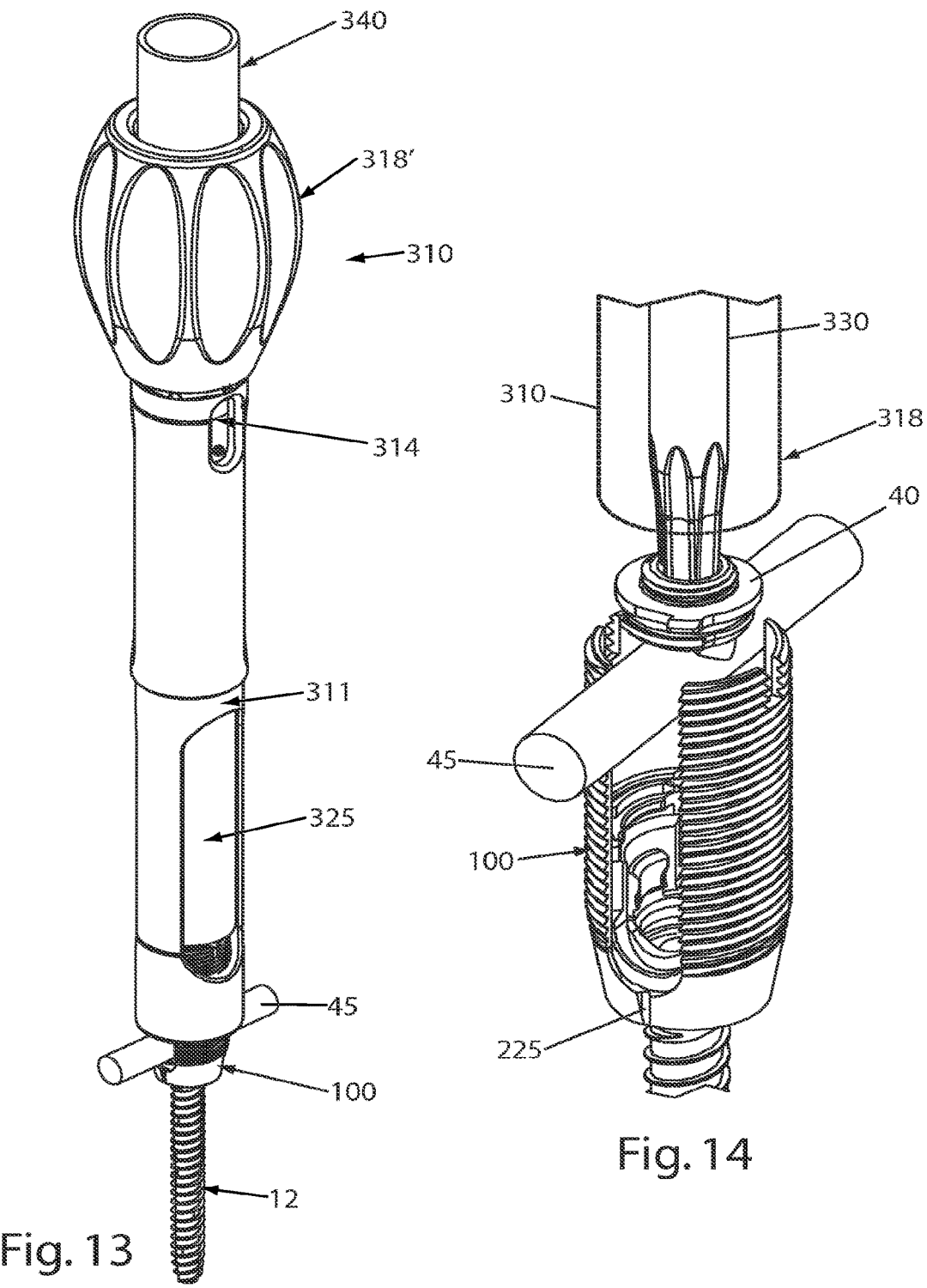
FIG. 13 is another perspective view of the reduction instrument.
FIG. 14 is a perspective view of another exemplary embodiment of a reduction instrument engaging the set screw or closure cap for urging the spinal rod into the reduction sleeve and bone fixation element.

As shown in FIG. 13, the reduction instrument 310 may also include a viewing window 325 formed in a side of the tube 311 to enable the surgeon to see the top of the reduction sleeve 100 and bone fixation element 10. In addition, the reduction instrument 310 may also include an indicator 327, more preferably an indicator line, to precisely indicate to the surgeon when the spinal rod 45 has been fully inserted into the rod-receiving channel 26 formed in the bone fixation element 10 to prevent over or under rotation.

Alternatively, as best shown in FIG. 14, the distal end 312 of the reduction instrument 310 may be sized and configured to receive and/or engage the set screw or closure cap 40 so that the set screw or closure cap 40 contacts and urges the spinal rod 45 into the rod-receiving channel 26 formed on the bone fixation element 10. Thus, eliminating the need for the separate set screw of closure cap screwdriver 330. It should be further noted that as shown in this exemplary embodiment, the reduction sleeve 100 has internal threads for engaging external threads formed on the reduction instrument 310. Alternatively, however, the reduction sleeve 100 could have external threads for engaging internal threads formed on the reduction instrument 310.

Figure 16:
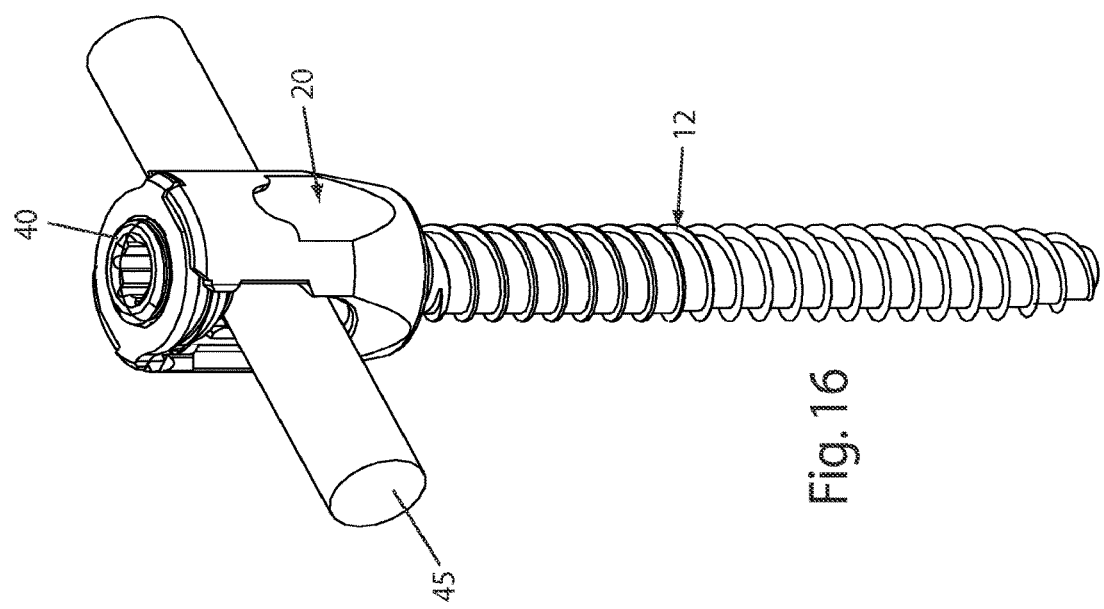
FIG. 16 is a perspective view of the spinal rod fully inserted and clamped in the bone fixation element with the reduction sleeve removed.
Figure 15:
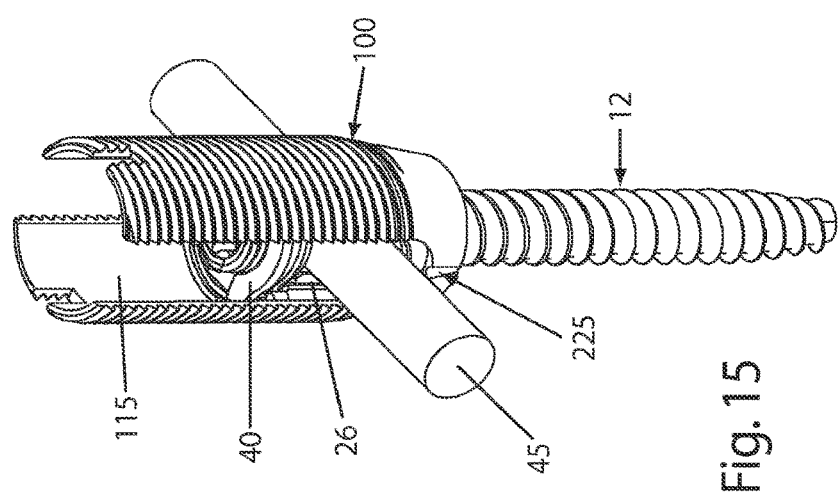
FIG. 15 is a perspective view of the reduction sleeve and bone fixation element with the spinal rod fully inserted and clamped in the bone fixation element.

As best shown in FIG. 15, once the spinal rod 45 has been secured within the rod-receiving channel 26 of the bone fixation element 10, the reduction instrument 310 may be removed. Next the reduction sleeve 100 may be removed by breaking the reduction sleeve 100 into multiple pieces at the break-off point 225 leaving the engaged bone fixation element 10 and clamped spinal rod 45, as shown in FIG. 16.

The reduction sleeve may be manufactured from any biocompatible material known in the art. The reduction sleeve may be manufactured from the same material as the bone fixation element or from a different material. The reduction sleeve may be manufactured from, but not limited to, titanium, titanium alloys, stainless steel, cobalt chromium, fibers, polymers, plastics, etc. Moreover, as will be generally understood by one of ordinary skill in the art, the reduction sleeve 100 may be provided in any number of sizes and configurations depending on the size and configuration of the bone fixation elements and spinal rods being used, which may be dependent on the type and location of the surgery being performed.

As will be appreciated by those skilled in the art, any or all of the components described herein such as, for example, the reduction sleeve, spinal rod, bone fixation elements, instruments, etc. may be provided in sets or kits so that the surgeon may select various combinations of components to perform a fixation procedure and create a fixation system which is configured specifically for the particular needs/anatomy of a patient. It should be noted that one or more of each component may be provided in a kit or set. In some kits or sets, the same device may be provided in different shapes and/or sizes (e.g., reduction sleeves of different sizes).

While the foregoing description and drawings represent the preferred embodiments of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are therefore to be considered in all respects as illustrative and not restrictive, the scope of the invention being indicated by the appended claims, and not limited to the foregoing description.

The invention claimed is:

1. A surgical method, comprising:
inserting a bone fixation element through a reduction sleeve, the bone fixation element having a head portion, a shank extending distally from the head portion, and a receiver in which the head portion is seated, wherein the bone fixation element is inserted into the reduction sleeve such that the shank extends through and is completely surrounded by a lower opening formed in the reduction sleeve and such that a tapered distal surface of the receiver abuts a corresponding tapered surface of the reduction sleeve, the lower opening being formed in the tapered surface of the reduction sleeve;
driving the shank of the bone fixation element into bone;
positioning a spinal rod in a rod-receiving channel of the reduction sleeve and a rod-receiving channel of the receiver; and
removing the reduction sleeve from the bone fixation element,
wherein positioning the spinal rod comprises advancing a reduction instrument along a threaded surface of the reduction sleeve to urge the rod into the rod-receiving channel of the receiver.

2. The method of claim 1, wherein the lower opening of the reduction sleeve is sized such that the receiver of the bone fixation element cannot fit through the lower opening.

3. The method of claim 1, wherein removing the reduction sleeve comprises breaking the reduction sleeve at a break-off point.

4. The method of claim 3, wherein the reduction sleeve comprises a pair of spaced apart arms joined by a bridge member, and wherein the break-off point is formed in the bridge member.

5. The method of claim 3, wherein the break-off point comprises opposed vertical grooves formed in the reduction sleeve distal to the rod-receiving channel of the reduction sleeve.

6. The method of claim 1, wherein advancing the reduction instrument comprises rotating the reduction instrument relative to the reduction sleeve about a longitudinal axis of the reduction sleeve.

7. The method of claim 1, further comprising inserting a set screw or closure cap through a central bore of the reduction instrument and securing the set screw or closure cap to the receiver.

8. The method of claim 1, further comprising polyaxially moving the shank of the bone fixation element relative to the reduction sleeve after inserting the bone fixation element through the reduction sleeve.

9. The method of claim 1, wherein inserting the bone fixation element comprises aligning an alignment flat of the receiver with an alignment flat formed in an interior of the reduction sleeve.

10. The method of claim 1, wherein inserting the bone fixation element comprises sliding a projection formed on one of the reduction sleeve and the receiver within a groove formed in the other of the reduction sleeve and the receiver.

11. The method of claim 1, wherein inserting the bone fixation element comprises positioning the receiver between the tapered surface of the reduction sleeve and an inwardly protruding ledge formed in the reduction sleeve.

12. The method of claim 1, wherein the reduction sleeve and bone fixation element are assembled as a single piece when the shank is driven into the bone.

13. The method of claim 1, wherein the lower opening is circular.

14. The method of claim 1, wherein the reduction sleeve includes first and second opposed arms, wherein the opposed arms are connected to one another only at a distal end thereof.

15. A surgical method, comprising:
inserting a bond fixation element through a reduction sleeve, the bone fixation element having a head portion, a shank extending distally from the head portion, and a receiver in which the head portion is seated, wherein the bone fixation element is inserted into the reduction sleeve such that the shank extends through a lower opening formed in the reduction sleeve and such that a tapered distal surface of the receiver abuts a corresponding tapered surface of the reduction sleeve in which the lower opening is formed;

driving the shank of the bone fixation element into bone;

positioning a spinal rod in a rod-receiving channel of the reduction sleeve and a rod-receiving channel of the receiver;

removing the reduction sleeve from the bone fixation element; and inserting a set screw or closure cap through a cap alignment tube having longitudinal slots sized and configured to receive and guide tabs of the set screw or closure cap into engagement with the receiver.

16. A surgical method, comprising:

inserting a bone fixation element through a reduction sleeve, the bone fixation element having a head portion, a shank extending distally from the head portion, and a receiver in which the head portion is seated, wherein the bone fixation element is inserted into the reduction sleeve such that the shank extends through a lower opening formed in the reduction sleeve, the receiver is entirely disposed within the reduction sleeve and such that a tapered distal surface of the receiver abuts a corresponding tapered surface of the reduction sleeve;

driving the shank of the bone fixation element into bone;

positioning a spinal rod in a rod-receiving channel of the reduction sleeve and a rod-receiving channel of the receiver; and removing the reduction sleeve from the bone fixation element;

wherein positioning the spinal rod comprises advancing a reduction instrument along a threaded surface of the reduction sleeve to urge the rod into the rod-receiving channel of the receiver.

17. The method of claim 16, wherein the reduction sleeve comprises a pair of spaced apart arms joined by a bridge member, and wherein removing the reduction sleeve comprises breaking the bridge member.

18. The method of claim 16, wherein advancing the reduction instrument comprises rotating the reduction instrument relative to the reduction sleeve about a longitudinal axis of the reduction sleeve.

19. The method of claim 16, wherein inserting the bone fixation element comprises aligning an alignment flat of the receiver with an alignment flat formed in an interior of the reduction sleeve.

20. The method of claim 16, wherein inserting the bone fixation element comprises sliding a projection formed on one of the reduction sleeve and the receiver within a groove formed in the other of the reduction sleeve and the receiver.

21. The method of claim 16, wherein the lower opening is circular.

22. The method of claim 16, wherein the reduction sleeve includes first and second opposed arms, wherein the opposed arms are connected to one another only at a distal end thereof.

* * * * *